United States Patent [19]
Kasvin et al.

[11] Patent Number: 6,102,344
[45] Date of Patent: Aug. 15, 2000

[54] ERGONOMIC DEVICE FOR ARM AND UPPER TORSO SUPPORT

[76] Inventors: Valery D. Kasvin; Karyn M. Kasvin, both of 16 Athlone Way, Menlo Park, Calif. 94025

[21] Appl. No.: 09/141,896

[22] Filed: Aug. 28, 1998

Related U.S. Application Data

[60] Provisional application No. 60/056,696, Aug. 28, 1997.

[51] Int. Cl.$^7$ .................................................. B68G 5/00
[52] U.S. Cl. .................................... 248/118; 248/125.9
[58] Field of Search .............................. 248/118, 118.3, 248/125.1, 125.9, 118.1, 130, 131, 289.11, 918, 125.8

[56] References Cited

U.S. PATENT DOCUMENTS

| | | | |
|---|---|---|---|
| 1,266,367 | 5/1918 | Wilson | 248/118 X |
| 2,028,979 | 1/1936 | Hintz | 248/118 X |
| 2,180,480 | 11/1939 | Richardson | 248/125.9 |
| 3,124,328 | 3/1964 | Kortsch | 248/118 |
| 3,269,981 | 8/1966 | Azim | 248/125.1 X |
| 4,706,915 | 11/1987 | Cindric et al. | 248/125.8 |
| 5,181,681 | 1/1993 | Edwards | 248/125.1 |
| 5,681,017 | 10/1997 | Clausen | 248/125.1 |

*Primary Examiner*—Ramon O. Ramirez
*Attorney, Agent, or Firm*—Jay P. Hendrickson, Esq.

[57] ABSTRACT

An ergonomic armrest primarily for use by dentists or dental hygienists permitting them to rest their arm on an armrest platter and to simultaneously rotate and revolve the platter so that they can perform an operation on a patient's teeth, while continuing to rest their arm. The bottom surface of the armrest platter is pivotally connected to the unsupported end of a cantilevered member, which is pivotally connected at its supported end to a rigid, but height adjustable, vertical support assembly.

15 Claims, 3 Drawing Sheets

ERGONOMIC DEVICE FOR ARM AND UPPER TORSO SUPPORT

This application relates to the Provisional application Ser. No. 60/056,696, filed on Aug. 28, 1997.

TECHNICAL FIELD

The present invention relates generally to the field of dentistry and more specifically to the improved arm and upper body supports for the use by dental professionals. In addition, the present invention may be used in any field to assist in reducing the static load on the upper extremities in persons working in a fixed position with very little posture variation.

BACKGROUND ART

The field of dental hygiene has changed significantly over the past several years. More hygienists are staying in the field longer, working more hours and performing more physically difficult procedures. These new work hazards, along with the necessary hazard of placing the body in fixed or awkward work positions, have caused an increase of musculoskeletal stress and injuries in the workplace.

Musculoskeletal pain in the neck and shoulders are reported in people who work in fixed awkward positions and/or have prolonged exposure to static or repetitive arm movement. The dental hygiene professional is exposed to all of these hazards, and the therefore dental hygienists are a group severely affected by musculoskeletal pain. In recent years, ergonomic studies have shown that musculoskeletal pain in the neck and shoulders is a major cause of work absence and workman's compensation claims. This pain can also interfere with patient care by diminishing the speed and quality of work. As more dental hygienists develop musculoskeletal problems, the physical, emotional and financial costs are becoming overwhelming.

The exact mechanism underlying work-related muscular pain syndrome is not yet fully understood. According to Swedish studies, the possible mechanisms may be related to high intramuscular pressures. This is true especially in muscles incased in narrow compartments (i.e. supra spinus muscle) or disturbances in the sympathetic regulation of muscular microcirculation (trapezium muscle). Other possible mechanisms include excessive load of small, low threshold motor units due to the lack of pauses or pain induced by vicious feedback loops which increases muscle tension leading to more pain. In work related muscle pain there are also reports of microscopic changes in type-1 (slow, fatigue resistant) muscle fibers.

The dental hygienist works with his/her arms in a position of abduction. The work may be classified as sitting or standing work within a limited space with time restraints. There are few pauses during treatment sessions and limited movements for extended periods of time. This may result in static muscle contractions (little or no change in extension or flexion of the muscle fibers), thus placing a prolonged musculoskeletal stress on the dental hygienist. These factors can contribute to muscular pain syndrome.

Considerable effort has been expended to prevent or to alleviate the muscular pain syndrome. In 1993, Tommy Oberg, MD, Phd, director and professional ergonomist in the Department of Biomechanics and Orthopedic Technology at the University College of Health Sciences, in Sweden, developed two ergonomic devices for the dental professional. He developed an operator chair with an attached armrest, as well as an attachment on the patient's headrest, to attempt to remedy the described work hazards of the dental hygiene profession However, Dr. Oberg's invention did not solve all the problems leading to muscular pain syndrome in dental hygienists. It did not provide the necessary support for the hygienist while positioned over the patient. Furthermore, the device of Dr. Oberg's invention is large and both devices are located in areas that would hamper the freedom of movement of the operator as well as being inconvenient for the patient. Dr. Oberg's invention is also cumbersome, expensive, and difficult to install. Finally, Dr. Oberg's devices are permanently fixed in one location. It does not allow for adjustment to cover all possible angles of the dental practitioner's work.

SUMMARY OF INVENTION

Accordingly, it is an object of the present invention to provide an ergonomic appliance for giving intermittent support to the operator's arm and weight of upper torso during treatment to alleviate musculoskeletal stress.

It is another object of the present invention to provide an ergonomic support that is easily adjustable to support the operators arm and upper torso during all phases of treatment.

It is another object of the present invention to provide an ergonomic support device, which is easy to install initially and, further, is locally mobile to permit addressing the patient from many directions.

It is further another object of this invention to provide a method for alleviating musculoskeletal stress and resulting musculoskeletal pain associated with prolonged awkward body positions in the health practitioner field.

The preferred embodiment of the present invention is a dental armrest device which permits the dentist or dental hygienist to rest his or her arm on a rotatable armrest platter while performing a dental operation for a patient. The bottom surface of the armrest platter is pivotally connected to the unsupported end of a cantilevered member, which is pivotally connected at its supported end to the upper end of a rigid vertical support assembly. The invention permits the armrest platter to rotate 360° in a horizontal plane around to its point of pivotal connection to the unsupported end of the cantilevered member and to revolve 360° in a horizontal orbit around the axis of the vertical support assembly. Preferably the arm support platter has an ergonomic shaped design to facilitate its use by the dentist or dental hygienist.

The main advantage of the present invention is that the operator's upper torso and arm can be supported while the arm is in abduction and in any position over and around the patient, regardless of the complexity of work being performed. As a result, the static pressure associated with musculoskeletal stress on the shoulder, neck and upper torso can be intermittently relieved, thereby reducing the potential for musculoskelatal problems as well as aiding in the recovery from injuries sustained from such stress.

A further advantage of the present invention is that it is easily adjustable and therefore it can easily adapt to different operatory environments, patient chairs and various weights and other physical characteristics of practitioners and patients.

A further advantage of the present invention is that it allows close proximity of the operator to the working area.

A further advantage of the present invention is that it can be simple to install.

Yet another advantage of the present invention is that it can be inexpensive to manufacture.

Still another advantage of the present invention is that it is comfortable for the patient and operator.

Another advantage of the present invention is that it may be quickly and easily moved to any position and is unobtrusive in use.

These and other objectives and advantages of the present invention will become clear to those skilled in the art and in view of the following descriptions. The descriptions include the best presently known mode for carrying out the invention and the industrial applicability of the preferred embodiments as described herein and as illustrated in the several figures of the drawing.

DETAILED DESCRIPTION OF THE INVENTION

The best presently known mode for carrying out the invention is a dental armrest device that can be easily positioned over and around the subject. The predominant expected usage of the armrest is in the field of dentistry but can be used in any situation that requires support of the arm when in an abducted position as well as support of the weight of the upper torso while performing long standing static of repetitive work.

Figure 1:
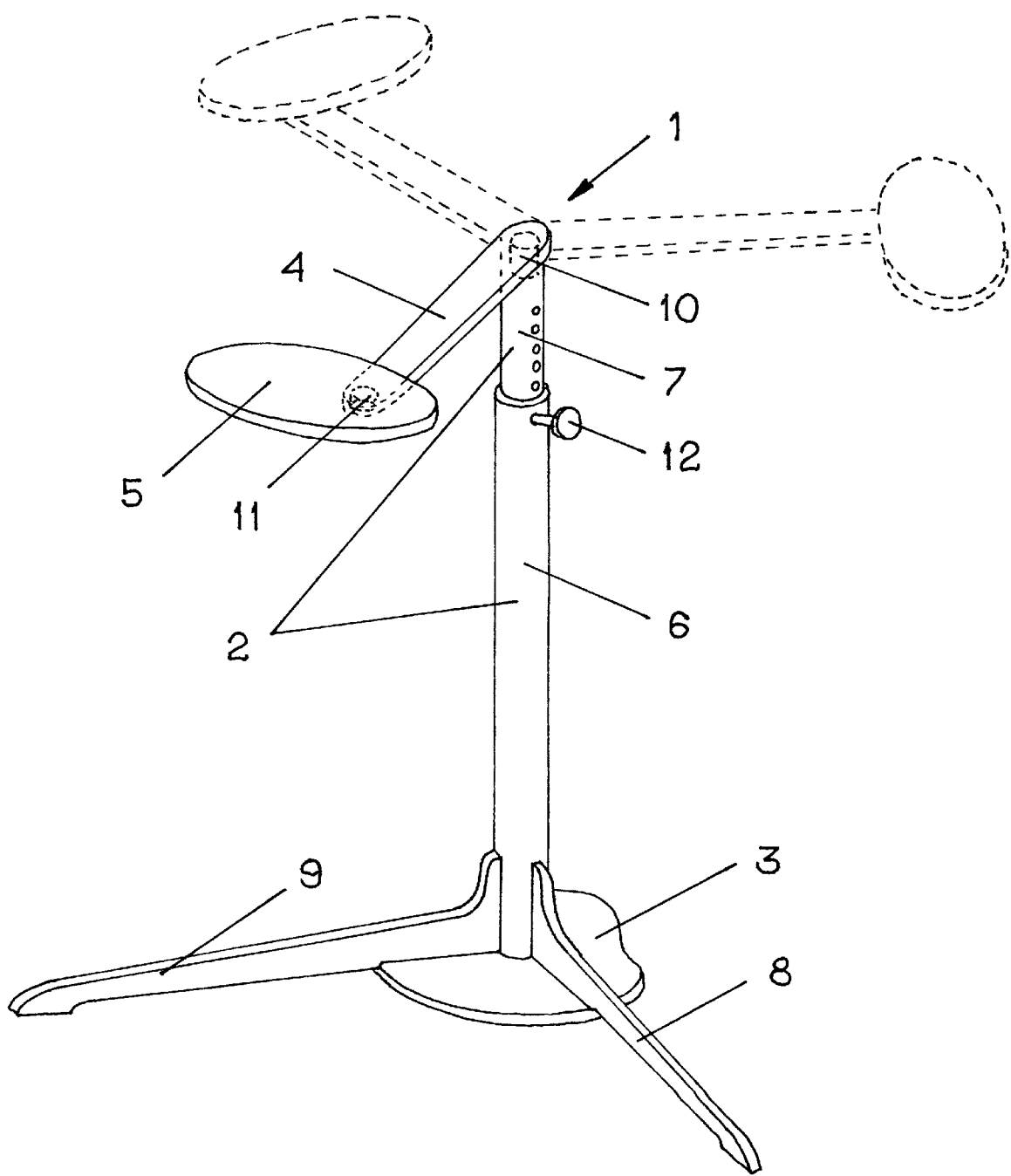
FIG. 1 is a full view of the armrest assembly illustrating the armrest platter in different positions.
Figure 2:
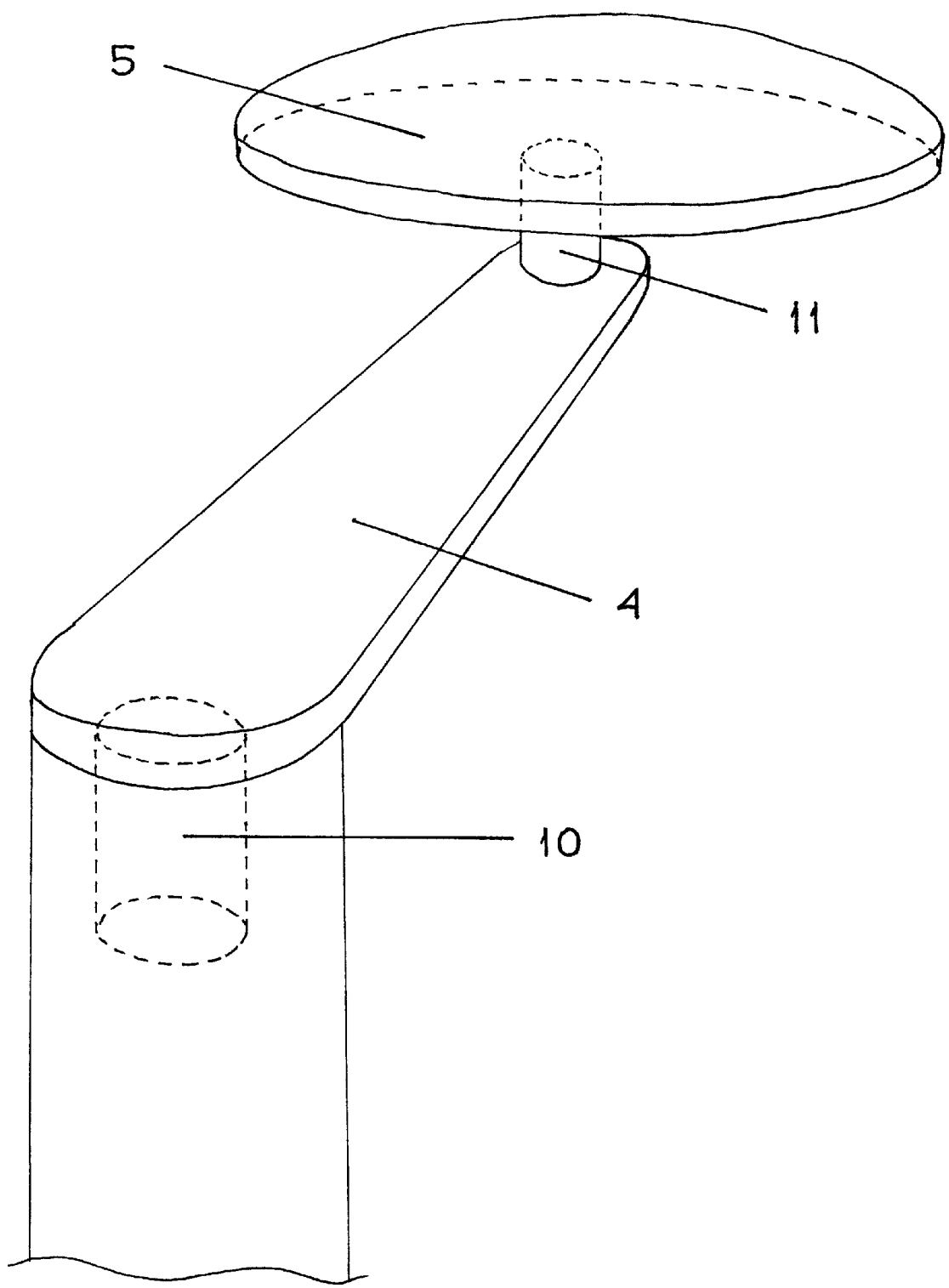
FIG. 2 is a partial view of the armrest assembly illustrating the location of the two pivot mechanisms.
Figure 3:
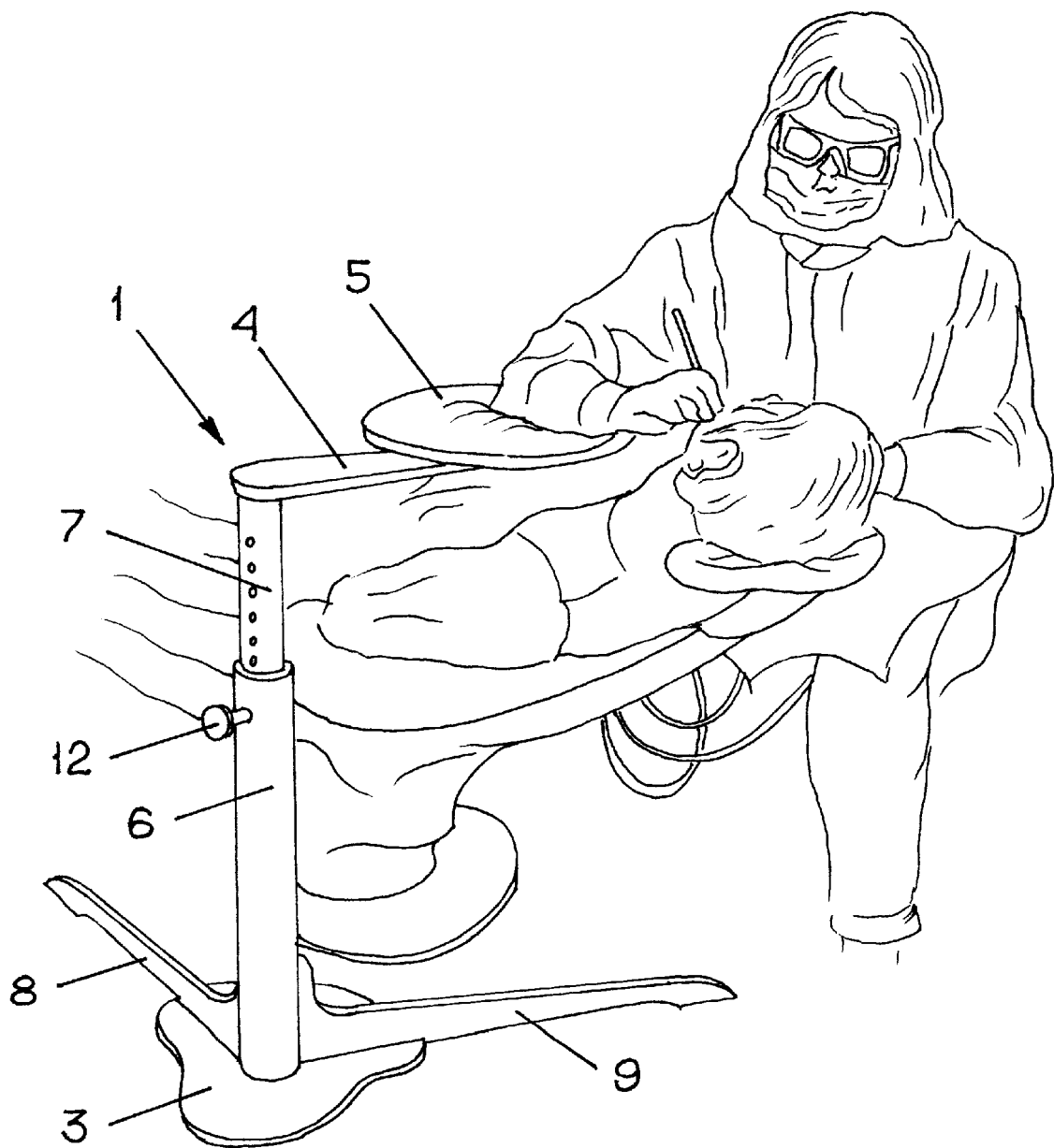
FIG. 3 is a full view of the armrest assembly in use.

The armrest device of the presently preferred embodiment of the present invention is illustrated in FIGS. 1–3.

The full view of the dental armrest assembly is illustrated in FIG. 1 and FIG. 3. Generally, the armrest device 1 comprises a rigid vertical support assembly, 2 including a base plate 3, a cantilevered member 4 and an armrest platter 5. In a preferred embodiment, the vertical support assembly 2 comprises an outer tube 6 and an inner tube 7, which is positioned concentrically within the outer tube 6. The bottom end of the outer tube 6 is secured to the top surface of the base plate 3 to form the rigid vertical support assembly 2. A pair of horizontal support legs 8 and 9 are each attached at one end to the bottom end of the outer tube 6 of the vertical support assembly 2, and each from the axis of the vertical support assembly. Preferably the support legs form a right angle to each other.

The upper end of the outer tube 6 of the vertical support assembly 2 contains an outer tube which extends through the wall of the outer tube 6. A plurality of similarly inner tube bores extend through the wall of the inner tube 7 and are aligned with the inner tube's axis. The armrest device 1 contains a first pivot mechanism 10 which pivotally connects the top end of the inner tube 7 of the vertical support assembly 2 to the supported end of the cantilevered member 4. The first pivot mechanism 10 permits the cantilevered member 4 to be rotated up to 360° in a horizontal plane around the axis of the vertical support assembly 2. A second pivot mechanism 11 pivotally connects the unsupported end of the cantilevered member 4 to the bottom surface of the armrest platter 5. The second pivot mechanism 11 permits the armrest platter 5 to rotate up to 360° in a horizontal plane around the second pivot mechanism 11. In combination the two pivot mechanisms enable the armrest platter 5 to rotate up to 360° around the second pivot 11 and to simultaneously revolve up to 360° in a horizontal orbit around the first pivot 10.

When using the armrest device 1, the height of the vertical support assembly 2 can be increased or decreased by means of a pin 12 which is passed through the outer tube bore simultaneously through one of the bores aligned with the outer tube bore. The need for use of the height adjustment is determined by whether the operator is sitting or standing and where the operator's arm is placed when the arm is in an abducted position away from the body and resting on the armrest platter 5 as shown in FIG. 3. The ability of the cantilevered member 4 to rotate up to 360° around the vertical support assembly 2 allows the operator to easily position his or her arm, which is resting on the top surface of the armrest platter 5, over and around the patient. Although the armrest platter 5 may be formed in many different shapes, in a preferred embodiment the armrest platter 5 is curved in shape and thin in width. Preferably, the armrest platter 5 has a thin foam padding and is covered with a material that is non-porous and easy to clean.

Various modifications may be made to the invention without altering its value or scope. For example, the materials used in construction can vary due to location of installment or cost factors.

The potential materials may include metals or plastic materials.

Other modifications may include the mode of attachment. The present invention can be freestanding (as pictured in FIGS. 1–3) with a single base or a multiple leg base, either stationary or with wheels for ease of transport. Other modes of attachment may include built into or bolted to either the patient or operators chair, or bolted to the floor, ceiling or walls of operatory.

The device used to adjust the height of the armrest may also be modified by use of hydraulics, crankshaft mechanism or any applicable technology. These may be operated either by hand, foot or remote control.

Additionally, the precise pivot mechanism may vary according to design application.

It is expected that this ergonomically designed armrest will be acceptable to the industry as a substitute for any existing device designed to relieve muscular pain caused during performance of static repetitive work. For these and other reasons, it is expected that the utility and industrial applicability of the invention will be both significant in the scope and of lasting duration.

Thus, the scope of the invention should be determined by the appended claims, and their legal equivalents, rather than by examples given.

We claim:

1. An armrest device comprising: a rigid vertical support member secured at its bottom end to a base; a cantilevered member pivotally secured at its supported end to the top end of the vertical support member, whereby the cantilevered member may be caused to rotate up to 360° in a horizontal plane around the axis of the vertical support member; and an armrest platter having a top and bottom surface, said bottom surface pivotally connected to the unsupported end of the cantilevered member, whereby the armrest platter provides dynamic support to an operator's arm, resting in an abducted position on the top surface of the armrest platter, due to the operator's ability to rotate the armrest platter up to 360° around its point of pivotal connection to the unsupported end of the cantilevered member, and to simultaneously revolve the armrest platter up to 360° in an orbit around the axis of the vertical support member.

2. The armrest device of claim 1 in which the base comprises a relatively flat plate with a top and bottom surface, said vertical support member's bottom end secured to the plate's top surface and the plate's bottom surface resting on a supporting surface.

3. The armrest device of claim 2 in which the base further comprises a plurality of horizontal leg members which are each secured at one end to the bottom end of the vertical support member.

4. The armrest device of claim 3 in which the plurality of horizontal leg members includes two leg members which are angularly separated by approximately 90°.

5. The armrest device of claim 1 in which the armrest platter is curved in shape and thin in width.

6. The armrest device of claim 1 in which the top surface of the armrest platter is covered with foam padding.

7. The armrest device of claim 6 in which the foam padding is covered with a non-porous material.

8. An armrest device comprising: a rigid vertical support assembly including an outer tube member, secured at its bottom end to a base, and an inner tube member, said inner tube member concentrically and slidably positioned within the outer tube member; the outer tube member having an outer bore through the wall of the outer tube member; the inner tube member having a duality of inner bores through the wall of the inner tube member; and a pin which is insertable through the outer bore and simultaneously through any one of the inner bores which is aligned with the outer bore, whereby the height of the vertical support assembly may be increased or decreased depending upon which inner bore is aligned with the outer bore a cantilevered member pivotally secured at its supported end to the top end of the inner tube member, whereby on the cantilevered member may be caused to rotate up to 360° in a horizontal plane around the axis of the inner tube member; and an armrest platter having a top and bottom surface, said bottom surface pivotally connected to the free end of the cantilevered member, whereby the armrest platter provides dynamic support to an operator's arm, resting in an abducted position on the top surface of the armrest platter, due to the operator's ability to use said arm to apply a slight horizontal force to the top surface of the armrest platter in order to rotate the armrest platter up to 360° around its point of pivotal connection to the free end of the cantilevered member, and to simultaneously revolve the armrest platter up to 360° in an orbit around the axis of the inner tube member.

9. The armrest device of claim 8 in which the base comprises a relatively flat plate with a top and bottom surface, said outer tube member's bottom end secured to the plate's top surface and the plate's bottom surface resting on a supporting surface.

10. The armrest device of claim 9 in which the base further comprises a plurality of horizontal leg members which are each secured at one end to the bottom end of the outer tube member and extend radially from the axis of the outer tube member.

11. The armrest device of claim 10 in which the plurality of horizontal leg members includes two leg members which are angularly separated by approximately 90°.

12. The armrest device of claim 8 in which the armrest platter is curved in shape and thin in width.

13. The armrest device of claim 8 in which the top surface of the armrest platter is covered with foam padding.

14. The armrest device of claim 13 in which the foam padding is covered with a non-porous material.

15. The armrest device of claim 8 further including a hydraulic means to adjust the position of the inner tube member.

* * * * *